(12) United States Patent  (10) Patent No.: US 8,568,324 B2
Roundhill                  (45) Date of Patent:     Oct. 29, 2013

(54) SYSTEMS AND METHODS FOR MECHANICAL TRANSLATION OF FULL MATRIX ARRAY

(75) Inventor: David N. Roundhill, Woodinville, WA (US)

(73) Assignee: Koninklijke Philips N.V., Eindhoven (NL)

( * ) Notice: Subject to any disclaimer, the term of this patent is extended or adjusted under 35 U.S.C. 154(b) by 290 days.

(21) Appl. No.: 12/680,333

(22) PCT Filed: Sep. 23, 2008

(86) PCT No.: PCT/IB2008/053871
§ 371 (c)(1),
(2), (4) Date: Mar. 26, 2010

(87) PCT Pub. No.: WO2009/040738
PCT Pub. Date: Apr. 2, 2009

(65) Prior Publication Data
US 2010/0217127 A1    Aug. 26, 2010

Related U.S. Application Data

(60) Provisional application No. 60/975,577, filed on Sep. 27, 2007.

(51) Int. Cl.
*A61B 8/00*     (2006.01)
(52) U.S. Cl.
USPC ........................................................ 600/444
(58) Field of Classification Search
USPC .................. 600/444, 459, 462–464, 466–471
See application file for complete search history.

(56) References Cited

U.S. PATENT DOCUMENTS

| 4,742,829 A | 5/1988 | Law |
| 5,090,414 A | 2/1992 | Takano |
| 5,191,890 A * | 3/1993 | Hileman ................ 600/463 |
| 5,379,772 A | 1/1995 | Imran |
| 5,957,850 A | 9/1999 | Marian |
| 6,059,731 A | 5/2000 | Seward |
| 6,419,633 B1 | 7/2002 | Robinson |

(Continued)

FOREIGN PATENT DOCUMENTS

| DE | 4423808 A1 | 1/1995 |
| DE | 102006056993 A1 | 6/2007 |
| WO | 2006119173 A1 | 11/2006 |

OTHER PUBLICATIONS

Daft, Chris et al "cMUTs and Electronics for 2D and 3D Imaging: Monolithic Integration, In-Handle Chip Sets and System Implication" Ultrasonics Symposium, vol. 1, Sep. 2005, pp. 463-474.

(Continued)

*Primary Examiner* — Elmer Chao

(57) ABSTRACT

An ultrasonic transducer assembly (10) for diagnostic imaging is provided. The ultrasonic transducer includes an elongated housing (12) that is configured and dimensioned to accommodate applicable anatomical constraints. The assembly includes a sensor assembly (20) that includes a two-dimensional matrix array of transducer elements (22) and a translation mechanism (32) to physically translate the two-dimensional matrix array of transducer elements (22) through a field of view of approximately 140 degrees by 80 degrees. An articulation control mechanism (38) allows a clinician to move the tip (14) of the ultrasonic transducer (10) into a desired imaging position, e.g., for fetal imaging.

11 Claims, 2 Drawing Sheets

(56) References Cited

U.S. PATENT DOCUMENTS

| | | | |
|---|---|---|---|
| 6,491,634 | B1 | 12/2002 | Leavitt et al. |
| 6,491,638 | B2 | 12/2002 | Oka |
| 6,589,179 | B2 * | 7/2003 | Criton et al. .......... 600/454 |
| 2003/0018269 | A1 | 1/2003 | Angelsen |
| 2003/0212327 | A1 * | 11/2003 | Wang et al. .......... 600/437 |
| 2005/0085730 | A1 * | 4/2005 | Flesch et al. .......... 600/459 |
| 2005/0119572 | A1 | 6/2005 | Angelsen |
| 2006/0036176 | A1 | 2/2006 | Angelsen |
| 2007/0038110 | A1 | 2/2007 | Flesch |
| 2010/0056921 | A1 * | 3/2010 | Rafter et al. .......... 600/447 |

OTHER PUBLICATIONS

Wygant, I.O. et al "Integrated Ultrasonic Imaging Systems based on CMUT Arrays; Recent Progress" Ultrasonics Symposium, vol. 1, Aug. 2004, pp. 391-394.

Noble, R.A. et al "A Cost-Effective and Manufacturing Route to the Fabrication of High-Density 2D Micromachined Ultrasonic Transducer Arrays and (CMOS) Signal Conditioning Electronics on the same Silicon Substrate" 2001 IEEE Ultrasonics Symposium Proceedings, vol. 2, pp. 941-944.

* cited by examiner

SYSTEMS AND METHODS FOR MECHANICAL TRANSLATION OF FULL MATRIX ARRAY

The present disclosure relates to transducer-based systems for ultrasonic diagnostic imaging systems. More particularly, the present disclosure is directed to ultrasonic transducer apparatus/systems and related methods that include and/or facilitate physically translating a two-dimensional phased array of transducer elements to provide enhanced diagnostic imaging.

Ultrasonic diagnostic imaging systems allow medical professionals to examine internal tissues and organs of patients without invasive exploratory surgery. Ultrasonic diagnostic imaging systems offer operational benefits as compared to other techniques that employ ionizing radiation, such as x-ray tomography. In addition, ultrasonic diagnostic imaging systems are generally less complex, and thus generally less costly, as compared to conventional imaging systems, such as magnetic resonance imaging and computed tomography systems.

Accordingly, ultrasonic diagnostic imaging systems offer significant advantages in numerous clinical settings, e.g., for monitoring fetal development. Ultrasonic fetal imaging can be performed by placing an ultrasonic transducer on the surface of a pregnant woman's abdomen and acquiring diagnostic data. Alternatively, ultrasonic fetal imaging can be performed transvaginally by introducing an ultrasonic transducer through a pregnant woman's vagina and acquiring diagnostic data.

Diagnostic imaging of a fetus in the first trimester of pregnancy has become a valuable tool in the potential detection of fetal anomalies. For example, It may be useful to identify potential anomalies early in the gestational cycle for improved care planning during the remainder of the pregnancy and/or to facilitate an early decision regarding the long-term viability of the pregnancy. A wide variety of potential anomalies presents a significant challenge to a clinician tasked with making a fetal diagnosis. Substantial portions of the fetal anatomy must be imaged with fine resolution to make such fetal diagnoses. For example, ultrasonic imaging to diagnose fetal heart anomalies requires both fine spatial and temporal resolution within a relatively small field of view whereas the field of view required for a transvaginal fetal examination, i.e., complete fetal anatomy, is substantially larger (approximately 140 by 80 degrees).

Since the mid 1990s, significant advances in the early diagnosis of fetal anomalies have been realized using transvaginal ultrasonic transducers employing high frequency, one-dimensional arrays of transducer elements. More recently, transvaginal ultrasonic transducers using 1 and so called "1.5" dimensional arrays have been mechanically translated to provide three-dimensional images.

However, current mechanically translated transvaginal ultrasonic diagnostic imaging systems have many limitations. For example, it is not possible to perform three-dimensional imaging of a fetal heart in real time without resorting to spatiotemporal image correlation techniques, which are not particularly robust. In addition, current techniques have a compromised ability to acquire color Doppler images while acquiring fetal heart images. Further, current transducers offer poor spatial resolution in the elevation plane of a mechanically translated one-dimensional array partially addressed by so-called "1.5" dimensional arrays (wherein the elevation dimension has a plurality of transducer elements, greater than one but substantially fewer than the longitudinal dimension. Additionally, the maternal anatomy generally limits transducer access, thereby affecting the ability to acquire necessary diagnostic data (which may be further limited depending upon the position of the fetus in the uterus).

The apparatus, systems and methods of the present disclosure address and/or overcome the issues noted above. Indeed, the present disclosure provides advantageous apparatus, systems and methods that facilitate mechanical translation of two-dimensional matrix transducer arrays for effective data capture in clinical environments. The disclosed apparatus, systems and methods have many clinical applications including, for example, in performing transvaginal fetal imaging.

The present disclosure provides advantageous methods, apparatus and systems for obtaining three-dimensional diagnostic images. According to exemplary embodiments, an ultrasonic transducer assembly is provided that includes an elongated housing configured and dimensioned so as to accommodate anatomical constraints, a sensor assembly mounted with respect to the housing that includes a two-dimensional phased array of transducer elements, and an articulation control mechanism that moves the two-dimensional phased array of transducer elements with respect to a target area. The sensor assembly is advantageously adapted for physical translation in situ to provide a clinically desirable field of view The elongated housing of the ultrasonic transducer assembly generally includes a tip portion, a base portion, and an intermediate portion disposed between the tip portion and the base portion. The sensor assembly is typically housed within (or with respect to) the tip portion of the elongated housing. In addition, the disclosed articulation control mechanism is generally positioned in or mounted, in whole or in part, with respect to the base portion of the elongated housing.

According to the present disclosure, a clinician is allowed to interact with or otherwise manipulate the articulation control mechanism. In exemplary embodiments of the present disclosure, when the articulation control mechanism is actuated by the clinician, a flexible intermediate portion associated with (or defined by) the elongated housing allows the tip portion to move relative to the base portion, thereby allowing optimal orientation of the transducer array with respect to a target area.

The disclosed sensor assembly generally includes a matrix array or two-dimensional phased array of transducer elements. The two-dimensional phased array of transducer elements is coupled to or mounted with respect to a translation mechanism that is adapted to pivot the array of transducer elements about or relative to an axis, thereby causing the transducer elements to move through a predetermined field of view. Sound waves are transmitted from the transducer elements and reflected (at least in part) by tissue or other anatomical structures in the target area. Reflected waves are received by the sensor assembly, which produces corresponding electrical signals that are transmitted to a processing unit where they are processed to generate a three-dimensional image, e.g., on a display. Thus, in advantageous implementations of the present disclosure, actuation/manipulation of the articulation control mechanism is effective to move the two-dimensional phased array of transducer elements with respect to the target area, thereby increasing the quality of the displayed image.

There are substantial advantages realized by exemplary embodiments of the present disclosure as compared to conventional ultrasonic transducer systems, e.g., transvaginal transducers. For example, the ability to effectively employ a translated matrix array—as permitted according to the present disclosure—permits acquisition rates sufficient for real time, three-dimensional volumetric imaging of desired anatomical structures, e.g., the entire fetal heart. More particularly, the mechanical motorized translation of the 2D array of the present disclosure affords the clinician a wide field of view to visualize the whole fetus, while the 2D array, when not being translated by the motorized mechanism, affords a high ultrasound image acquisition rate within a smaller field of view that is optimally suited for imaging the fetal heart, an organ that is rapidly beating (170 beats per minute is typical). The present disclosure permits advantageous articulation of the tip to permit visualization of the full extent of the relevant anatomy.

Of note, the three-dimensional image data acquired with the disclosed matrix transducer arrays can be suitable for ancillary data processing technologies. For example, such three-dimensional data may be augmented with color Doppler information to show blood flow through the vessels of the fetal heart. However, as is known in the art, Doppler processing can only be performed on acoustic data that is specifically acquired for that purpose, thereby requiring multiple transmit/receive cycles along the same direction.

While particular embodiments of ultrasonic transducer assemblies made in accordance with the present disclosure may be used with desirable results for transvaginal fetal imaging, it will be recognized that the present disclosure is not so limited. As will be appreciated by one of ordinary skill in the art, ultrasonic transducer assemblies made in accordance with the teachings herein can be employed in many different types of diagnostic imaging, including prostate imaging, laparoscopic diagnostic imaging, and other clinical applications.

It is to be understood that both the foregoing general description and the following detailed description are exemplary and are intended to provide further explanation of the disclosed apparatus, systems and methods. The accompanying drawings, which are incorporated in and constitute part of this specification, are included to illustrate and provide a further understanding of the disclosed apparatus, systems and methods. Additional advantageous features, functions and benefits of the disclosed apparatus, systems and methods will be apparent from the description which follows, particularly when read in conjunction with the accompanying figures.

To assist those of skill in the art in making and using the disclosed transducer assemblies and related methods, reference is made to the accompanying figures, wherein.

In accordance with the exemplary embodiments of the present disclosure, an ultrasonic transducer assembly is provided for anatomical imaging, e.g., transvaginal fetal imaging, that includes a physically translatable, two-dimensional array of transducer elements adapted for articulation for placement for enhanced diagnostic fetal imaging. In fetal imaging implementations of the disclosed ultrasonic transducer assembly, the two-dimensional array of transducer elements are adapted for articulation within a patient's vagina. Alternative clinical implementations may be developed according to the present disclosure, wherein articulation of a two-dimensional array of transducer elements facilitates enhanced capture of imaging data.

Figure 1:
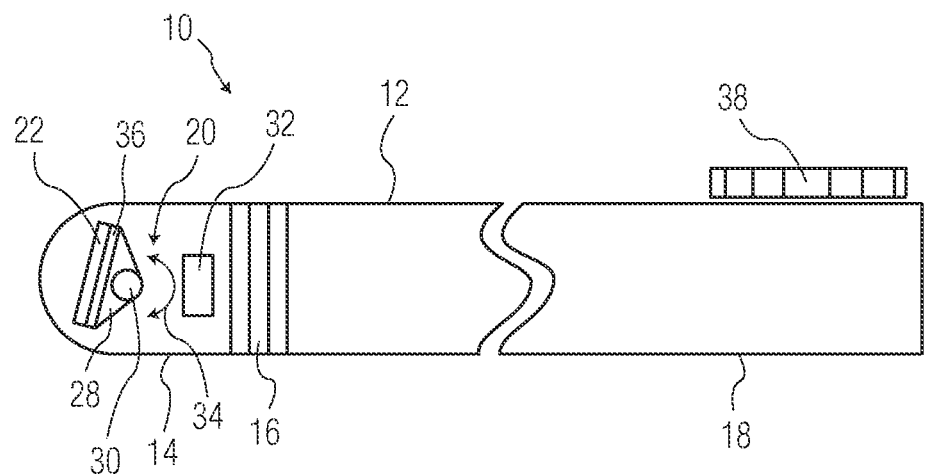
FIG. 1 is a schematic depiction of an exemplary ultrasonic transducer assembly made in accordance with the present disclosure.

Referring now to FIG. 1, an exemplary ultrasonic transducer assembly is generally indicated at 10. The ultrasonic transducer assembly 10 includes an elongated housing 12 that is configured and dimensioned to accommodate applicable anatomical constraints, e.g., maternal anatomical constraints associated with fetal imaging applications hereof. The elongated housing 12 includes a tip portion 14, an intermediate portion 16, and a base portion 18.

The tip portion 14 houses and/or supports a transducer assembly 20 that includes a matrix array of transducer elements 22. The matrix array is generally planar or substantially planar in geometry, although alternative geometric configurations may be employed without departing from the spirit or scope of the present disclosure. The matrix array of transducer elements is also referred to herein as a two-dimensional phased array of transducer elements 22. The individual transducer elements (not illustrated) extend in both an azimuth dimension, which is indicated by arrow 24 in FIG. 2, and an elevation dimension, which is indicated by arrow 26 in FIG. 2. Various transducer element designs may be employed according to the present disclosure. For example, individual transducer elements may be piezoelectric elements arranged as disclosed in U.S. Pat. No. 6,419,633. The design and/or selection of appropriate transducer elements for incorporation into the disclosed matrix array is well within the skill of persons of ordinary skill in the art based, inter alia, on applicable operational, structural and/or clinical parameters.

The two-dimensional phased array of transducer elements 22 is typically attached or mounted with respect to a transducer mount 28. The transducer mount 28 is pivotally attached with respect to a translation axis 30. A translation mechanism 32 is provided that includes a stepper motor (not illustrated) that is used to physically translate the two-dimensional phased array of transducer elements 22 by pivoting the transducer mount 28 about the translation axis 30, as indicated by arrow 34. The transducer mount 28 is driven by the stepper motor, which could be coupled to the transducer mount 28 through appropriate linkage mechanism(s), e.g., a geared linkage (not illustrated), a belt drive (not illustrated), or a combination of the two.

Under clinician control, the translation mechanism 32 causes the two-dimensional phased array of transducer elements 22 to "wobble" back and forth, thereby sweeping out a field of view of approximately 140 degrees. Thus, in an exemplary implementation of the present disclosure, an external control module (not illustrated) is adapted to send/transmit control signals to the stepper motor, e.g., using wireless communication media or through control wires (not illustrated), thereby causing the two-dimensional phased array of transducer elements 22 to be physically translated through a field of view during ultrasonic imaging. The field of view through which the two-dimensional phased array of transducer elements 22 are translated may be predetermined, e.g., subject to known angular limitations, residence times, translation speeds and the like.

In exemplary embodiments of the present disclosure, transducer assembly 20 includes sub-beamformer electronics 36 to minimize the number of signals that are communicated between the transducer assembly 20 and external processing equipment (not illustrated). For example, U.S. Pat. No. 6,491,634 discloses similar sub-beamformer electronics designed for a one-dimensional array of transducer elements.

With continued reference to FIG. 1, the base portion 18 includes an articulation control mechanism 38 that may be actuated to move the two-dimensional phased array of transducer elements 22 in a direction that is into or out of the page. In exemplary embodiments, the articulation control mechanism 38 may be a knob coupled through the elongated housing 12 to a gear assembly (not illustrated), which is also coupled to the base of the tip portion 14. When a user actuates the articulation control mechanism 38 by turning the knob, the tip portion 14 moves with respect to the base portion 18. For example, when the user moves the articulation control mechanism 38 in a clockwise direction, the tip portion 14 moves in a direction that is into the page, and when the user moves the articulation control mechanism 38 in the opposite direction, the tip portion 14 moves in a direction that is out of the page.

In other exemplary embodiments, the articulation control mechanism 38 may be coupled through the housing 12 to an electronic switch (not illustrated) that is electronically connected to a stepper motor (not illustrated) that is coupled (directly or indirectly) to the transducer assembly 20. When the user actuates the articulation control mechanism 38 in a clockwise direction, the stepper motor moves the transducer assembly 20 in a direction that is into the page. Similarly, when the user actuates the articulation control mechanism 38 in the opposite direction, the stepper motor moves the transducer assembly 20 in a direction that is out of the page.

Figure 2:
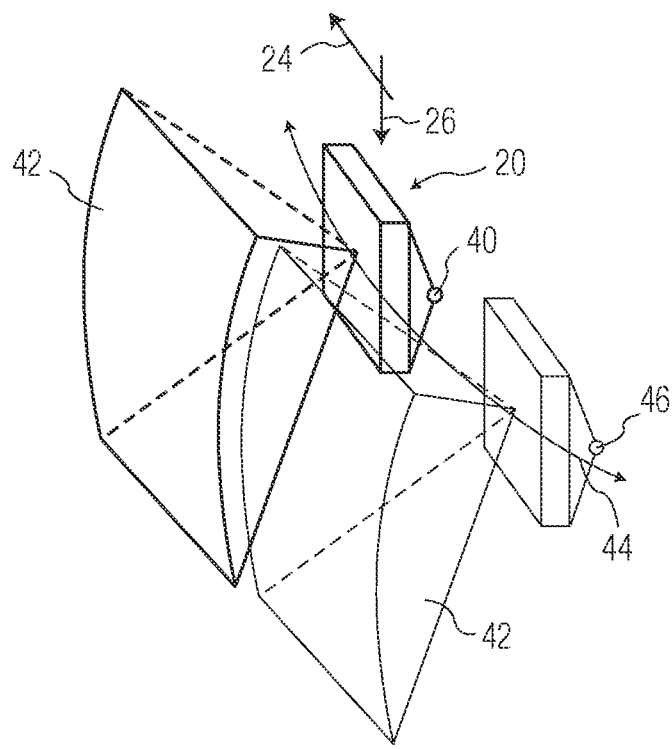
FIG. 2 illustrates matrix array articulation of the exemplary ultrasonic transducer assembly of FIG. 1.

Referring now to FIG. 2, exemplary articulation of the two-dimensional phased array of transducer elements 22 is illustrated. Transducer assembly 20 is shown in an unarticulated state, wherein the center of the transducer assembly 20 is initially located at position 40. The two-dimensional phased array of transducer elements 22 acquires data in a three-dimensional volumetric region 42. Although not illustrated in FIG. 2, the three-dimensional volumetric region 42 is translated as the translation mechanism 32 (shown in FIG. 1) moves the two-dimensional phased array of transducer elements 22 through a field of view, e.g., a predetermined field of view.

With further reference to the schematic depiction of FIG. 2, the articulation control mechanism (shown in FIG. 1) has been actuated, causing the transducer assembly 20 to move along an articulation path 44, which results in the center of the transducer assembly 20 moving to position 46. Articulation of the transducer assembly 20 causes the three-dimensional volumetric region 42 to shift as shown. In this way, a user/clinician is able to steer the three-dimensional volumetric region 42 toward an area of interest and acquire high resolution ultrasound data in that area.

Figure 3:
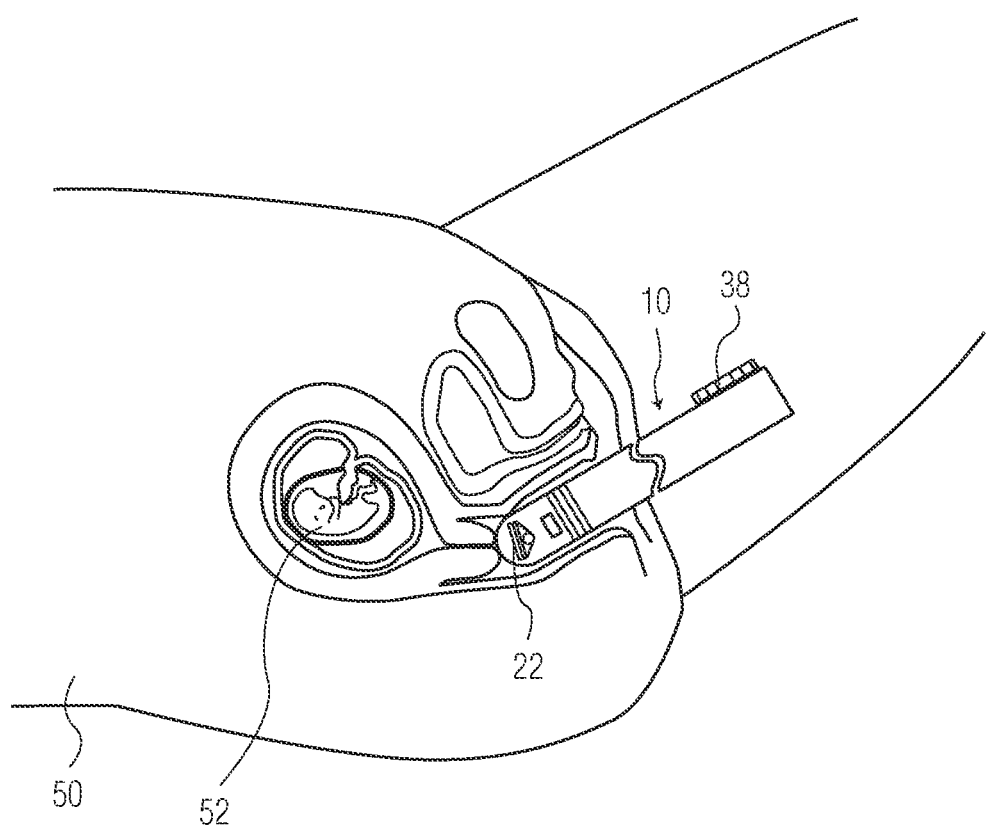
FIG. 3 illustrates the exemplary ultrasonic transducer assembly of FIG. 1 positioned for transvaginal fetal imaging.

Referring now to FIG. 3, a transvaginal diagnostic imaging application using exemplary ultrasonic transducer 10 is illustrated. The ultrasonic transducer 10 is positioned for transvaginal imaging of a fetus 52 within patient 50. Assuming for purposes of this example that the heart of the fetus 52 is positioned on the right side of the patient 50, a medical professional/clinician (not illustrated) may actuate the articulation control mechanism 38 to move the two-dimensional array of transducer elements 22 along with the three-dimensional volumetric region of ultrasound data acquisition (see FIG. 2) toward the right side of the patient 50 to obtain higher resolution images of the heart of the fetus 52.

The apparatus, systems and methods presented herein may be used for a broad range of ultrasonic diagnostic imaging applications. Devices made in accordance with the teachings of the present disclosure are particularly well suited for high resolution ultrasonic diagnostic fetal imaging. A significant advantage of ultrasonic transducers made in accordance with the present disclosure, among other things, is the enhanced diagnostic imaging capabilities achieved by physically translating a two-dimensional array of transducer elements. The present disclosure thus provides ultrasonic transducer assemblies that have, inter alia, a relatively small, two-dimensional array of transducer elements packaged into a small transducer housing resulting in a small ultrasonic transducer with a relatively wide field of view. Articulation of the transducer tip allows optimal positioning of the two-dimensional array of transducer elements for improved imaging.

Although the present disclosure has been described with reference to exemplary embodiments and exemplary applications, the present disclosure is not limited thereby. Rather, the disclosed apparatus, systems and methods are subject to various changes, modifications, enhancements and/or alternative applications without departing from the spirit or scope of the present disclosure. Indeed, the present disclosure expressly encompasses all such changes, modifications, enhancements and alternative applications herein.

The invention claimed is:

1. A transvaginal ultrasonic transducer assembly, comprising:
    an elongated housing having a principal axis and that includes a tip portion, an intermediate portion, and a base portion;
    a transducer assembly comprising a two-dimensional phased array of transducer elements extending in an azimuth dimension and an elevation dimension perpendicular to said azimuth dimension which is mounted on a transducer mount having a translation axis oriented generally perpendicular to the principal axis of the housing, said transducer mount and two-dimensional phased array of transducer elements disposed within the tip portion of said elongated housing, the two-dimensional phased array of transducer elements configured to transmit and receive sound waves within a three-dimensional volumetric region positioned in front of the tip portion in a direction opposite a direction of the base portion and which can be pivoted about the translation axis; and
    a translation mechanism configured for physically translating said transducer mount about the translation axis within the elongated housing while the elongated housing remains substantially rigid, so as to translate the three-dimensional volumetric region in which the two-dimensional phase array transmits and receives sound waves so as to sweep out a clinically desirable field of view in a first direction relative to the principal axis; and
    an articulation control mechanism configured to cause the transducer assembly to move along an articulation path extending in a second direction relative to the principal axis, wherein the movement along the articulation path is done by flexing the intermediate portion which allows the tip portion to move relative to the base portion.

2. The transvaginal ultrasonic transducer assembly according to claim 1, wherein the articulation control mechanism is further configured to position the translation axis at one position along the articulation path that is perpendicular to the principal axis defined by said elongated housing.

3. The transvaginal ultrasonic transducer assembly according to claim 1, wherein the two-dimensional phased array of transducer elements is a planar matrix array.

4. The transvaginal ultrasonic transducer assembly according to claim 1, wherein the elongated housing is configured and dimensioned to accommodate anatomical constraints.

5. The transvaginal ultrasonic transducer assembly according to claim 1, further comprising sub-beamforming electronics in electrical communication with said two-dimensional phased array of transducer elements; said sub-beamforming electronics being translated by said translation mechanism.

6. The transvaginal ultrasonic transducer assembly according to claim 5, wherein said articulation control mechanism is configured to control articulation of said two-dimensional phased array of transducer elements relative to said elongated housing in a direction that is substantially perpendicular to the principal axis of the base portion of said elongated housing.

7. A method for performing intracavity ultrasonic diagnostic imaging, comprising the steps of:
providing an ultrasonic transducer assembly in the tip portion of an elongated housing that includes the tip portion, an intermediate portion, and a base portion, wherein the tip, intermediate, and base portions are disposed along a principal axis of the elongated housing, the ultrasonic transducer assembly further including a two-dimensional phased array of transducer elements disposed within the tip portion, said two-dimensional phased array of transducer elements extending in an azimuth dimension and an elevation dimension perpendicular to said azimuth dimension, the two-dimensional phased array of transducer elements further being configured to transmit and receive sound waves within a three-dimensional volumetric region positioned in front of the tip portion, along the principal axis, in a direction opposite a direction of the base portion; and
physically translating said two-dimensional phased array of transducer elements about a translation axis within the elongated housing while the elongated housing remains substantially rigid, with a translation mechanism in a first direction different from the direction of the principal axis and moving the transducer assembly along an articulation path in a second direction different from the direction of the principal axis with an articulation control mechanism to translate the three-dimensional volumetric region in which the two-dimensional phase array transmits and receives sound waves so as to provide a clinically desirable field of view via the translation mechanism, wherein the two-dimensional phased array of transducer elements is coupled to the translation mechanism, wherein the movement along the articulation path is done by flexing the intermediate portion which allows the tip portion to move relative to the base portion.

8. The method for performing ultrasonic diagnostic imaging according to claim 7, wherein said translating step includes physically translating said two-dimensional phased array of transducer elements about a translation axis that is perpendicular to the principal axis of said elongated housing.

9. The method for performing intracavity ultrasonic diagnostic imaging according to claim 7, further comprising the step of displaying a thick slice view using data acquired in an elevation dimension.

10. The method for performing intracavity ultrasonic diagnostic imaging according to claim 7, wherein moving the transducer assembly along an articulation path further comprises the step of physically articulating, via the articulation control mechanism, said two-dimensional phased array of transducer elements relative to the principal axis of said elongated housing toward a target area.

11. The method for performing intracavity ultrasonic diagnostic imaging according to claim 10, wherein said articulating step includes physically articulating said tip portion relative to the principal axis of said elongated housing with respect to a target area.

* * * * *